United States Patent [19]

Zale et al.

[11] Patent Number: 5,310,688

[45] Date of Patent: May 10, 1994

[54] METHOD AND APPARATUS FOR ELUTING PROTEINS IN AFFINITY MEMBRANE PROCESS

[75] Inventors: Stephen E. Zale, Uxbridge; Clark K. Colton, Newton, both of Mass.

[73] Assignee: Sepracor Inc., Marlborough, Mass.

[21] Appl. No.: 35,549

[22] Filed: Mar. 23, 1993

Related U.S. Application Data

[63] Continuation of Ser. No. 487,668, Mar. 2, 1990, abandoned, which is a continuation-in-part of Ser. No. 428,263, Oct. 26, 1989, which is a continuation-in-part of Ser. No. 265,061, Oct. 31, 1988, abandoned.

[51] Int. Cl.⁵ .................. G01N 33/545; B01D 15/08; B01D 61/00
[52] U.S. Cl. ..................................... 436/535; 436/531; 436/177; 436/178; 210/500.21; 210/634; 210/639; 435/180; 435/182
[58] Field of Search ............... 436/501, 518, 531, 532, 436/535, 807, 823, 824, 178, 548; 435/180, 181, 182; 210/500.21, 634, 639

[56] References Cited

U.S. PATENT DOCUMENTS 4,693,985  9/1987  Degen et al. .................... 436/531

OTHER PUBLICATIONS

Brandt, S. Bio/Technology (1988) 6:779–782.
Neil et al, Protein Purification Methods, A Practical Approach (ELV Harris & S. Angal, ed.) 1989, Oxford University Press, New York, N.Y., pp. 282–290.
Hansen et al. Proc Natl Acad Sci USA, 79:2788–2792, (1982).
Herrmann et al. J. Biol. Chem, 254(18):8713–8716, (1979).
Lennon et al. J. Biol. Chem, 255(10):4395–4398, (1980).
C. Ostlund, Trends in Biotech., 11:288–293 (1986).
H. A. Chase, Chem. Eng. Sci., 39:1099–1125 (1984).
T. Kristiansen, In: Affinity Chromatography, O. Hoffman-Ostenhof (Ed.), Pergamon Press, Oxford, U.K., pp. 191–206 (1978).
D. Bureau and J. Daussant, J. Immunol. Methods, 41:387–392 (1981).
K. K. Andersson et al., J. Immunol. Methods, 25:375–381 (1979).
D. Bureau and J. Daussant, J. Immunol. Methods, 57:205–213 (1983).
R. F. Murphy et al., Biochem. Biophys. Acta, 420:87–96 (1976).

Primary Examiner—Margaret Parr
Assistant Examiner—Carla J. Myers

[57] ABSTRACT

This invention relates to methods and apparatus for carrying out affinity separations of proteins under conditions optimized for recovering biologically active protein. The method utilizes a membrane-bound ligand first to capture and separate a ligate from a fluid mixture and subsequently to release said ligate in purified form. The present methods enhance the yield of active ligate recovered in the process. The invention has particular relevance to the recovery and purification of proteins from mixtures.

4 Claims, 1 Drawing Sheet

METHOD AND APPARATUS FOR ELUTING PROTEINS IN AFFINITY MEMBRANE PROCESS

RELATED APPLICATIONS

This is a continuation of copending application Ser. No. 07/487,668 filed on Mar. 2, 1990, now abandoned, Which is a continuation-in-part of copending U.S. application Ser. No. 07/428,263 filed Oct. 26, 1989, which is a continuation-in-part of Ser. No. 07/265,061 filed Oct. 31, 1988, now abandoned; the entire disclosure of each is incorporated by reference herein. Also incorporated by reference herein is prior copending U.S. application Ser. No. 07/258,406 filed Oct. 17, 1988, now abandoned.

BACKGROUND OF THE INVENTION

Affinity Separations

Of the separation technologies available today, those based on affinity interactions are ever more popular, particularly at the laboratory scale. Affinity separation has become the preferred method for purifying proteins and other biomolecules from complex, biologically derived fluids. *Affinity Chromatography and Biological Recognition*, I. M. Chaiken, M. Wilchek and I. Parikh (eds.), Academic Press, New York, 1983; Hill, E. A. and M. D. Hirtenstein, "Affinity chromatography: its application to industrial scale processes", *Advances in Biotechnological Processes*, Alan R. Liss, Inc., New York, 1983). The key to the method's attractiveness is its unequaled degree of selectivity.

Affinity separations, as they are conventionally practiced, typically involve a number of sequential steps. First, a solution containing a component to be separated from the solution (a component of interest) is passed through a column containing a highly specific ligand which will reversibly bind the compound of interest immobilized on a support, usually high-surface-area beads or particles. As the fluid passes through the column in this loading step, the desired component binds selectively and reversibly to the immobilized ligand, while most impurities pass unhindered. Residual impurities are removed by flushing the column with an appropriate buffer solution in a subsequent washing step. The component, now purified but still bound to the immobilized ligand, is then recovered by passing an eluent solution through the column that has the effect of disrupting the ligand-to-ligate binding interaction. Generally, the pH, concentration of a salt, or some other chemical characteristic of this eluent solution is altered significantly from the corresponding values of the loading and wash solutions, and it is this change that is responsible for weakening the affinity interaction and thereby causing desorption and elution of the ligate molecule.

Many types of molecules can serve as ligands, including antibodies, antigens, enzyme inhibitors, isolated receptors, and more recently, cloned receptors. Bailon, P. et al., *Bio/Technology* 5:1195 (1987). In contrast, however, the choice of materials to support the ligand has been somewhat limited. Agarose gel beads (e.g., 50 to 150 microns diameter) have traditionally received the most attention as affinity ligand supports, particularly on the laboratory scale. Within recent years, cross-linked and accordingly more rigid versions of these and other polysaccharide-based gel beads have been developed and introduced, as have various microporous support particles based on synthetic polymer compositions. These polymeric support materials are now complemented by various inorganic materials. For example, porous silica packed in high-pressure columns is used to perform affinity separations in an HPLC-like process. Typical pore diameters in the silica support range from about 200 to about 1000 Angstroms, whereas silica particle diameters are generally in the range of about 5 to 25 microns.

Affinity Membranes

Affinity separation processes for the recovery and purification of proteins are conventionally carried out using sorbent beads or particles packed in columns, as discussed above. The adsorption process is carried out in a cyclical fashion comprising four steps:

1. Load: A solution of target component in a mixture is made to pass through a packed column; target component ("ligate") is recognized and captured by the immobilized sorbent ("ligand"), while most contaminants pass through.
2. Wash: A wash solution is passed through the column to flush out contaminants present in the column void volume as well as to displace non-specifically bound contaminating substances.
3. Elute: An eluent solution is passed through the column to disrupt the affinity binding between immobilized ligand and reversibly bound ligate, causing elution of the latter from the column in a purified condition.
4. Regenerate: A regeneration solution is passed through the column in order to return it to conditions (e.g., pH and/or ionic strength) that favor ligand/ligate binding.

Despite the high selectivity that affinity processes provide, however, their application on the process scale has been hampered by the inability of affinity columns to handle high flowrates at reasonable ligand utilization efficiencies.

Affinity membrane devices are based on microporous membranes, preferably hollow fibers activated by covalent attachment of affinity ligands to the interior surfaces of the membrane's pore walls. In operation, feed solution is made to flow through the membrane from one of its surfaces to the other, during which process the target molecule is recognized and captured by the immobilized ligand which it encounters, leaving the filtrate devoid of ligate. Like columns, these affinity membranes can be operated in a cyclic affinity adsorption process to produce high-purity protein in a single step. However, unlike columns based on particulate affinity ligand supports, affinity membranes are not hampered by the serious pressure drop and mass transfer limitations from which columns suffer. As a result, affinity membranes are capable of operating at higher volumetric throughputs and ligand utilization efficiencies than are columns.

Both polymeric and inorganic affinity support particles suffer from hydrodynamic or pressure drop limitations when used in columns. With the former (e.g., soft agarose gel beads), particle compressibility is a problem, inasmuch as attempts to increase flowrate through a column packed with agarose are normally met by increased pressure drops. This leads in turn to further compression of the particles and reduced bed permeability. Clonis, Y.D., *Bio/Technology* 5:1290(1987). It is only by resorting to very shallow but large-diameter packed columns (i.e., columns with a relatively large ratio of bed diameter to depth) that practical volumetric throughputs can be obtained. Alternatively, one can resort to more rigid particles (e.g., silica, controlled-pore glass), but here the small size of the support particles limits volumetric throughput unless high operating pressure is employed.

In contrast, affinity membranes with adsorptive pore walls provide extremely short fluid-flow path lengths in comparison to the superficial area provided for flow. This unique geometry of affinity membranes thus leads to very high fluid throughputs per unit of applied pressure difference as compared to affinity columns.

Another important consideration in evaluating the merits of membranes vs. columns as affinity ligand supports is the matter of their relative mass transfer efficiency. Efficient capture of a target protein in an affinity column requires that the characteristic time for diffusion of protein to the immobilized ligand be short as compared to the residence time of fluid in the column. If this condition is not met, premature breakthrough is encountered and the "dynamic" sorption capacity of the bed will not approach its "static" or equilibrium capacity.

A characteristic diffusion time for the encounter between diffusing ligate and immobilized ligand can be defined as the ratio of the square of a characteristic diffusion distance to the diffusivity of the ligate molecule. The required residence time of fluid in the affinity device during the loading step will increase in proportion to this characteristic diffusion time. Thus, in order to keep the characteristic distance for ligate diffusion into the support as small as possible (and thereby to maximize device throughput during loading), it is necessary to use support particles that are as small as practical (e.g., fine silica or synthetic polymeric particles). However, doing so tends to aggravate the above-mentioned pressure drop problem, forcing one away from low-pressure operation towards a high-pressure liquid chromatography process.

In contrast, affinity membranes obviate the need to work with small (e.g., micron-sized) particles in order to minimize diffusion distances and diffusion times. Where protein-containing solutions are pumped across affinity membranes, the characteristic distance across which ligate must diffuse in order to meet membrane-bound ligand is of the order of a quarter of the pore diameter; typically, this diffusion distance is only a fraction of a micron. Because diffusion time varies with the square of diffusion distance, the impact of the reduction in diffusion distance afforded by affinity membranes on improved mass transfer efficiency and volumetric productivity is dramatic. These and other aspects of affinity membrane performance have been discussed by S. Brandt et al., *Bio/Technology* 6:152 (1988) and in copending U.S. applications Ser. No. 07/265,061 and No. 07/428,263, referred to above.

THE ELUTION STEP IN AFFINITY SEPARATIONS

Eluents for use in displacing bound ligates in affinity chromatographic processes can be categorized as either specific or non-specific. *Affinity Chromatography: Principles & Methods*, Pharmacia LKB Biotechnology, Uppsala, Sweden, (1979). Specific methods for displacing antigens from immunoadsorbents rely on supplying a free hapten or an analogue as an eluting agent; its function is to compete with the antigen for the binding site of the immobilized antibody, thus causing its desorption. Non-specific methods for desorption and elution generally rely on a change in pH frequently to a value of 2.5 or below (e.g., with glycine-HCl or propionic acid) and/or the addition of polarity reducing agents (e.g., dioxane or ethylene glycol), denaturants (e.g., urea or guanidine hydrochloride), and chaotropic ions (e.g., trifluoroacetate, thiocyanate, etc.). In addition to elution at low or acidic pH values, protein bound to immunoadsorbents can also be eluted at alkaline pH values (e.g., up to pH 11) as well as with in high-ionic-strength buffers at elevated, basic pH values (as per the above-cited Pharmacia monograph).

The above-cited monograph by Pharmacia provides a concise listing of representative eluents (see particularly Table 7.1 on page 94) and a discussion of their respective modes of action. Similar eluents and elution techniques find use in other types of affinity chromatography which are not based on immobilized antibodies. Examples include recovery of IgG's by immobilized protein A and related ligands (e.g., protein G, protein A/G hybrids), as well as other adsorption methods (e.g., hydrophobic interaction and ion-exchange chromatography) that are not based on biological affinity between ligate and ligand. For example, it is known that elution of IgG's from protein G and other proprietary IgG-binding ligands can require elution pH values as low as 1.5–2.0, at which conditions denaturation of the target protein frequently occurs.

It is commonly recognized that one of the most significant drawbacks of conventional column affinity separation processes is the fact that dissociation of the ligand-ligate complex can be difficult to accomplish. This is especially true in immunoaffinity chromatography, since the dissociation constants of many antigen-antibody complexes are particularly low. Lowe, C. R. and P. D. G. Dean, *Affinity Chromatography*, Wiley & Sons, London, (1974); and Ostlund, C., *Trends in Biotech.* 11:288–293 (1986). Accordingly, harsh solutions containing high concentrations of acid, base, chaotropes, and/or denaturing agents must frequently be employed in the elution step if the elution step is to be accomplished in a reasonable period of time. Chase, H. A., *Chem. Eng. Sci.* 39:1099–1125 (1984).

These harsh elution conditions have the particular disadvantage in protein purification of often causing denaturation and inactivation of eluted proteins (such as tissue plasminogen activator (tPA), IgG's and IgM's) with the result that much of their mass, but only a fraction of their full biological activity, is recovered in the process. Kristiansen, T., *Affinity Chromatography*, O. Hoffman-Ostenhof, ed., Pergamon Press, Oxford, pp. 191–206 (1978). Denaturation of therapeutic proteins may lead to formation of partially denatured and "foreign" contaminants in a preparation, as well as to partial or complete loss of the intended and desired in vivo function of the therapeutic protein. Thus, the use of harsh elution conditions and the protein denaturation caused by them seriously effect not only product quality but also process economics.

Lastly, resort to extreme elution conditions may also have adverse effects on the stability and lifetime of an immobilized affinity ligand, reducing the number of purification cycles over which it exhibits a useful binding capacity. Frequently, immobilized ligand life will be sensitive to extremes of pH and/or high concentrations of specific or non-specific eluents. As an example, it has been shown that the rate of leaching of a lectin ligand immobilized on a Sepharose gel increases with increasing concentrations of both specific (D-galactose) and non-specific (D-glucose) displacing sugars in the eluent buffer employed. Walzel, H. et al., *Biomed. Biochim. Acta.* 4:221 (1989). Thus, longer immobilized lectin life can be accomplished by using lower eluting sugar concentrations. Since certain types of affinity ligands (e.g., monoclonal antibodies) are very costly, the increased frequency of ligand replacement associated with the use of harsh elution conditions can represent an intolerable processing cost. Olson, W. C. and M. L. Yarmush, *Biotech. Progress* 3:177–188 (1987).

Several prior-art methods for avoiding extreme elution conditions have been developed. Generally speaking, these involve either manipulating the nature of the eluent or the affinity ligand, or they involve novel elution driving forces. Bureau, D. and J. Daussant, *J. Immunol. Methods* 41:387–392 (1981). Elution techniques based on relatively gentle eluents are exemplified by the use of organic solvents and basic media (Andersson, K. K. et al., *J. Immunol. Methods* 25:375 (1979)), and by the use of distilled water. Bureau, D. and J. Daussant, *J. Immunol. Methods* 57:205–213 (1983). Alternatively, relatively weakly binding ligands (e.g., antibodies with relatively large dissociation constants) may be employed (Erikson, R. P. and E. Steers, (1970), *Arch. Biochem. Biophys.* 137:399), as may chemically modified antibody ligands. Murphy, R. F. et al., *Biochim. Biophys. Acta* 420:87 (1976). Finally, electrophoretic elution methods are being studied for their potential in facilitating the removal of ligate from ligand at mild conditions. Olson, W. C. and M. L. Yarmush, *Biotech. Progress* 3:177–188 (1987); Schulze-Osthoff, K. et al., *Anal. Biochem.* 177:314–317 (1989). While many of these prior-art methods do indeed provide improvements in recovery of functional ligate, none of these strategies is without its disadvantages. Some are limited in terms of the scope of ligands and ligates for which they are applicable; others require excessive volumes of eluent; and still others (e.g., electroelution) involve additional process complexity and cost.

In summary, it is commonly known that the potential benefits of conventional column affinity chromatography are frequently overshadowed by the need to employ harsh elution conditions (e.g., extremes of pH) which can cause significant losses in recovery of active protein and/or reduce the effective lifetime of the affinity ligand. At the same time, the use of membranes as affinity ligand supports has been shown to provide certain advantages in affinity separations (e.g., high volumetric productivity, efficient use of ligand, and scaleability) that are related to the unique aspect ratio of membranes relative to conventional columns and to their superior mass transfer characteristics.

SUMMARY OF THE INVENTION

The present invention relates to a method for carrying out affinity membrane separations of biological material under conditions which are optimized for recovering biologically active material and maintaining affinity ligand activity, particularly, where the ligate and/or the ligand is a protein sensitive to pH extremes and/or high concentrations of eluting solutes.

In one embodiment of the present method, a pH sensitive ligand or ligate, such as an acid-sensitive ligate which is associated with a membrane-bound ligand, such as an acid-sensitive ligand, is contacted with an eluent having a pH which is from about 0.5 to about 1.0 pH units more neutral than the pH of an eluent necessary to optimally elute the ligate from a non-membrane support matrix, such as Sepharose, agarose, controlled-pore glass or silica gel. The term "associated with" as used herein generally means that the ligate is bound to the ligand. Due to the properties obtainable in affinity separations with microporous membranes much milder elution conditions can be used. For example, a milder eluent having a pH of from about 2.5 to about 6.0 is used in the membrane affinity system, wherein an eluent having a pH of from about 1.5 to about 5.0 would be necessary to elute same protein from a conventional non-membrane support matrix.

In another embodiment of the present method, a pH-sensitive ligate associated with the membrane-bound ligand is contacted with a strong (acidic or basic) eluent, comparable to that used in non-membrane systems, but the amount of time the eluent remains in contact with the ligate and with the membrane is minimized. Total elution time is preferably less than a minute, with the residence time of elution buffer in the membrane matrix being limited to about 30 seconds or less, and preferably no longer than about 2 to 10 seconds. This rapid elution technique allows the desired ligate to be quickly and efficiently separated from the ligand while minimizing its contact with the acidic eluent. Alternatively, the rapidity of elution from affinity membrane supports can also be measured in terms of a space velocity expressed as volumes of solution passed through the membrane matrix per unit volume and unit time. Whereas the affinity membranes of the present invention can be operated during elution at space velocities as high as about 15–20 reciprocal minutes ($min^{-1}$), more conventional gel-type (e.g., crosslinked agarose) and silica-based affinity columns are typically operated at space velocities of between about 0.05 to 0.25 $min^{-1}$ and 0.1 to 0.5 $min^{-1}$ respectively.

In another embodiment of the present method, the pH-sensitive ligate is contacted with a strong acidic or basic eluent capable of dissociating the ligate from the membrane-bound ligand and then immediately contacting the ligate which is in the eluent with a neutralizing buffer having a pH of from about 6 to about 8.5 or with a basic or acidic solution capable of neutralizing the acidic eluent and thus bringing its pH to a value of about 6 to 8.5. The neutralizing buffer quenches the acidic or basic action of the eluent, and prevents it from degrading the pH-sensitive ligate.

The present method is based on the discovery that it is possible to exploit the unique characteristics of affinity membranes for the purpose of improving yields of active product and useful ligand life in cases where the product or ligand would otherwise be degraded by harsh elution conditions. The present method provides a membrane-based affinity system which enhances yields of active proteins in the elution step of affinity separation processes, and which improves the fractional recovery of biologically active and functional protein attainable in affinity separations.

BRIEF DESCRIPTION OF THE FIGURE

The FIGURE is a schematic illustration of a representative affinity separation system. The bold lines and arrows indicate a process which can be used in a quenched elution.

DETAILED DESCRIPTION OF THE INVENTION

Figure 1:
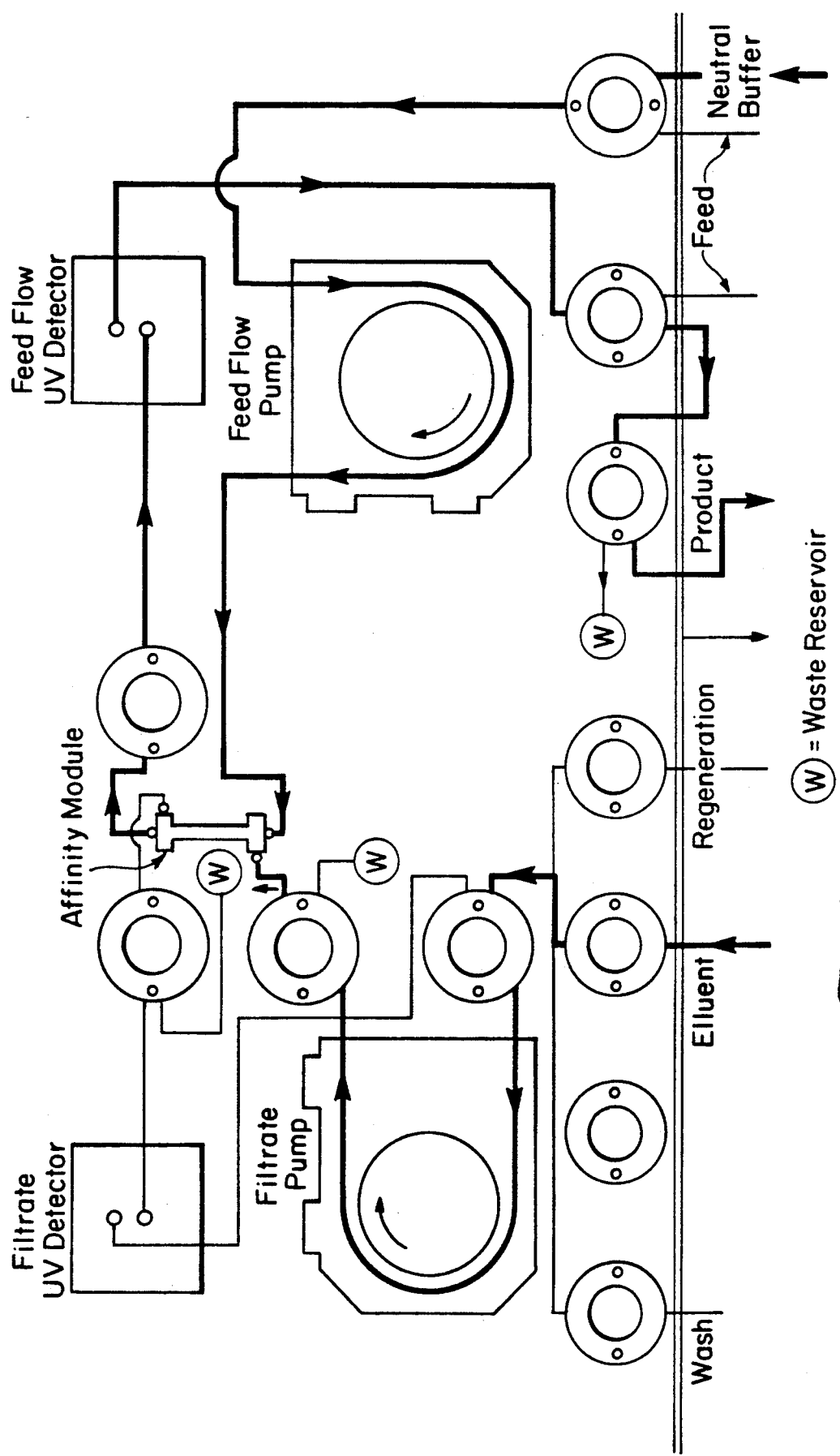

The present invention is a method of separating biologically active material, particularly proteins sensitive to pH extremes and/or high concentrations of eluting solutes, which relies on the unique characteristics of affinity membranes, and conditions adjusted to minimize inactivation and/or degradation of the protein separated from a solution. In this section, the basic elements of an affinity membrane system are described, along with a recitation of the various steps involved in its use in purifying a protein from a complex biological mixture according to the method of the present invention. It will prove convenient to describe the method and apparatus of this invention in terms of its application to protein purification using protein A as the ligand. However, one could equally well have chosen to illustrate the method and apparatus by describing use of another ligand, such as another binding protein (e.g., a monoclonal antibody) as the immobilized ligand in an immunoaffinity purification process. The focus here on "bioaffinity" purification is an appropriate one, since both ligates (e.g., therapeutic proteins) and ligands (e.g., monoclonal antibodies) can be sensitive to the harsh eluents sometimes required to reverse their binding to one another. However, it should be recognized that the scope of the invention set forth herein is a good deal broader, encompassing other types of ligates (especially labile ones) and strongly binding ligands.

Additionally, for the sake of definiteness the invention will be described here in terms of an instrument suitable for bench- and preparative-scale purification processes which is schematically illustrated in the FIGURE. However, it should be recognized that the present invention is also applicable to and particularly useful in process-scale protein purification operations, wherein the equipment will be larger but the basic processing steps will remain essentially the same.

As mentioned above, there are four phases in the membrane affinity purification process, namely, loading, washing, elution, and regeneration. These four phases can further be broken down into the 10 steps enumerated in Table I.

TABLE 1

STEPS IN THE AFFINITY MEMBRANE PURIFICATION PROCESS

| Phase | Step Number | Step Name |
|---|---|---|
| Loading | 1 | Feed Solution Loading |
| Washing | 2 | Shell Wash |
| Washing | 3 | Lumen Wash I |
| Washing | 4 | Lumen Wash II |
| Elution | 5 | Shell Flush |
| Elution | 6 | Pre-Elution |
| Elution | 7 | Main Elution |
| Elution | 7a | Quenched Elution |
| Elution | 8 | Post-Elution |
| Regeneration | 9 | Shell Flush Regeneration |
| Regeneration | 10 | Lumen Flush Regeneration |

Because of the number of steps and their short duration, it is convenient to perform them with the aid of a semi-automated instrument. An instrument which is useful in the present method is described in detail in copending U.S. patent applications Ser. No. 07/265,061 and Ser. No. 07/428,263, and incorporates, among other things, the following components:

an affinity membrane module and feed and filtrate pumps (e.g., peristaltic pumps) for delivery of fluids to and from the membrane device;

feed and filtrate UV detectors for on-line measurement of total protein concentration;

various switching valves, fluid reservoirs, and interconnecting tubing; and a controller capable of directing the sequence and timing of the several steps involved in the purification cycle.

The basic operations conducted in an affinity membrane purification process are largely as set forth in co-pending U.S. applications Ser. Nos. 07/265,061 and 07/428,263 and further described below. Subsequent sections of the present application then describe various embodiments of the present invention as they relate to improved apparatus and methods for protein elution. In particular, the techniques of "mild elution", "rapid elution", and "quenched elution" are described in detail herein.

Affinity Membrane Purification Method and Apparatus

Biological products are captured by an affinity membrane module through formation of reversible complexes between ligand molecules immobilized on the pore wall surfaces of the membrane and biomolecules in solution. Particularly useful as affinity membranes are microporous hollow-fiber membranes, e.g., porous membranes comprised of a polysulfone-containing substrate material coated with a hydrophilic material and subsequently activated for covalent attachment of a ligand. Prior copending U.S. application Ser. No. 07/258,406 filed Oct. 17, 1988 describes the preparation of a suitable microporous hollow-fiber membrane, along with various procedures for coating, activating, and linking various ligands to it. For monoclonal antibody (IgG) capture and purification, protein A ligand can be attached to the interior membrane surfaces using, for example, fluoromethylpyridinium p-toluenesulfonate linking chemistry, as well as other chemistries that are well known in the art of affinity chromatography.

Without wishing to be limited as to module size, typical affinity membrane modules range in size from 1.5 mL to 1 L total volume. The 1.5 mL and 30 mL modules are particularly preferred for use in conjunction with the automated apparatus described herein, whereas 150 mL and 1 L modules are more suited to process-scale applications.

The feed to the affinity membrane process may consist of practically any protein-containing fluid; examples include mammalian cell culture supernatants, ascites fluids, fermentation broths, or blood and blood plasma. This fluid will generally be at near-neutral pH and otherwise physiological conditions. Pretreatment or clarification of the fluid by various standard methods (e.g., microfiltration) may be required in order to prevent excessive membrane fouling.

A typical purification process will employ at least three buffer solutions:

1. Wash Buffer: e.g., 0.1M phosphate-buffered saline (PBS), pH 8, which flushes the system in the washing phase;
2. Elution Buffer: e.g., 0.1M citrate, pH 3, which is used in the elution phase to induce a pH change and so release the bound IgG;
3. Regeneration Buffer: e.g., 0.1M PBS with 0.1% Tween (PBST), which restores the system to neutral pH at the end of the purification cycle.

It should be noted that the particular buffer compositions recited above are meant solely to serve as examples; they are not limiting as to the practice of the process of the present invention. The following steps can be better understood by referring to the FIGURE.

Loading (Step 1)

To begin the purification cycle, IgG is loaded onto the membrane-bound protein A ligand while the system is at pH 7. Cell culture fluid containing IgG is circulated from the feed reservoir through the affinity module (shown in the FIGURE) at a preset rate. As IgG passes through the affinity membrane, it binds to the immobilized ligand. In the module, the fluid divides into two paths, referred to as the shell and lumen paths. The lumen path is followed by that portion of the feed fluid that does not pass through the membrane but that flows out the affinity module through the lumen outlet (indicated in the FIGURE by the bold line and arrow from the top of the affinity module), still carrying its original concentration of IgG. This undepleted fluid returns to the feed reservoir for recycling and eventual recovery of the IgG contained within it. The shell path is used to describe the path of the fluid entering the affinity module which is drawn through the hollow-fiber membrane wall by the filtrate pump. This fluid loses its IgG to the protein A ligand, so that it emerges from the shell-side surface of the membrane devoid of much or all of its IgG. This filtrate is now pumped from the shell outlet (indicated in the FIGURE by the line from the right side at the top of the affinity module) of the affinity module to the waste reservoir at the preset rate.

During this loading phase, the filtrate flowrate (shell path) is always less than the feed flowrate (lumen path). Both UV detectors operate in the loading phase, providing a continuous record of the absorbance (and hence total protein concentration) of both feed and filtrate streams as they emerge from the module.

Washing (Steps 2-4)

Unbound IgG remaining in the affinity module may be washed out with PBS buffer in a three-part process. In the shell wash the shell (external) side of the hollow fibers is washed to remove any remaining IgG-depleted cell culture (or other) fluid. PBS is drawn by the filtrate pump into the shell inlet (indicated by the bold line and arrows entering the lower left side of the affinity module) and out the shell outlet, subsequently to be routed to the waste reservoir.

The operation of the affinity purification system during the lumen washes (Steps 3 and 4) is as described below; in these steps, the lumen (internal) side of the hollow fibers is washed free of cell culture fluid. PBS is drawn by the filtrate pump into the shell inlet, through the membrane, out the lumen outlet, and then past the feed UV detector. In the first lumen wash (Lumen Wash I), residual cell culture (or other) fluid returns to the feed reservoir for eventual capture of the IgG that it contains. In the second lumen wash (Lumen Wash II), the wash fluid is directed to the waste reservoir.

Elution (Steps 5-7)

IgG is released from the protein A ligand in a series of elution steps. Citrate buffer drops the system pH to about 3, causing release of IgG from protein A. Product is eluted during each of the steps of this phase, but generally it is collected only during the main elution step (or, alternatively, the "quenched" elution step which is described below).

In the shell flush step the system is prepared for a drop from about pH 7 to about pH 3. Citrate eluent drawn by the filtrate pump flows in the shell inlet, flushes out PBS, and then flows through the shell outlet to the waste reservoir.

During pre-elution, release of IgG begins as citrate eluent drawn by the filtrate pump flows into the affinity module through the shell inlet, through the membrane, and out the lumen outlet. Fluid then flows to the waste reservoir, passing the feed UV detector along the way.

A subsequent post-elution step conducted after the main elution step discussed below is similar, with eluent here being directed to the waste reservoir as release of IgG falls from peak levels. The fluid follows the same path as in the pre-elution step to the waste reservoir.

During the main elution step, when a 1.5 mL affinity membrane module is in place, approximately 8-9 mL of product-bearing fluid is released from the ligand; during this step, the ligate release rate reaches its maximum value. Eluent follows the same path as in the previous step, but it now flows to the product reservoir for collection rather than to the waste reservoir for disposal.

Regeneration (Steps 9 and 10)

The affinity purification system is restored to neutral pH in this step by flushing with PBST buffer in a two-part sequence. All material is flushed to the waste reservoir.

In the shell regeneration step, the shell-side volume in the follow-fiber affinity membrane module is restored to neutral pH as PBST is drawn by the filtrate pump into the shell inlet and out the shell outlet.

In the subsequent lumen flush regeneration step, the lumenal volume of the hollow-fiber module is restored to neutrality. PBST is drawn by the filtrate pump into the shell inlet, through the membrane, and out the lumen outlet, thus preparing the affinity purification system to begin another purification cycle.

Examples of protein purification by this affinity membrane method and apparatus are found in prior copending U.S. application Ser. Nos. 07/265,061 and 07/428,263 (see in particular Sections 6.1-6.6 and 6.11 therein).

Release of Bound Protein at Mild Elution Conditions

In exploring the operating limits of the affinity membrane purification apparatus discussed in the preceding section (and shown in the FIGURE), it was discovered that it is possible to displace ligand-bound protein at substantially milder elution conditions than those which are typically required with more conventional gel- and particulate-type affinity media used in packed columns and stirred tanks. This unexpected ability to elute protein ligates from affinity membranes at significantly milder elution conditions than heretofore possible has an important benefit, namely, that higher yields of protein and longer lifetimes for the immobilized ligand can be realized with affinity membrane purification in cases where either the protein being recovered or the ligand being employed or both are labile at the relatively harsh elution conditions that would normally be employed in conventional affinity chromatography techniques, i.e., a pH of about 1.5 to about 3, or a pH of above about 10.

For example, elution of IgG from particulate or bead-type chromatographic media activated with protein A is frequently effected by contacting the matrix with an acidic solution, typically, 0.1M citrate buffer at pH 3.0, glycine/HCl buffer at pH 2.5, phosphate-citrate buffer at pH 2.8, or 1M propionic acid. With protein G and other proprietary IgG-binding ligands, elution pH values as low as 1.5 may be required. The same or similar eluents can also be used in affinity membrane purification, as has been described above. If the protein undergoing purification is not sufficiently acid stable, however, these acidic elution conditions can cause an undesirable loss of biological activity of the product. The need clearly exists for affinity separation methods that permit milder elution of proteins from protein A and other affinity supports.

Unexpectedly, it has been found that protein can be eluted from affinity membrane matrices at significantly milder conditions than the same protein can be eluted from particulate supports in packed-column operations. For example, it has been discovered that the pH of the elution buffer employed in an affinity membrane purification of pH sensitive proteins can be at least from about 0.5 to 1.0 pH units more neutral than the pH of the elution buffer that provides equivalent eluting power in a conventional column affinity process.

This phenomenon may be understood in a general way if it is realized that the contribution of diffusion towards observed rates of association and dissociation of proteins to and from the affinity support matrix is minimized in affinity membrane separations. As discussed above, solutions are convected through the pores of a microporous affinity membrane; hence, diffusion distances are on the order of a fraction of the pore diameter. Because diffusional hindrances that may limit rates of dissociation of bound proteins are minimized, it is reasonable to expect that it may be possible to elute proteins from affinity membranes under milder conditions than those required for elution of porous bead affinity supports. In the present mild elution method, for example, the protein can be eluted by contacting the membrane-bound ligand-ligate pair with an eluent having a pH of from about 6 to about 2.5.

Rapid Elution from Affinity Membrane Supports

These same considerations suggest that elution from affinity membrane supports might be effected significantly more rapidly than from affinity columns when elution buffers of equivalent eluting strength are employed. In particular, if the same elution pH is used in both affinity membrane and affinity column processes, then the arguments set forth in the preceding paragraph would suggest that free ligate might diffuse away from the surface of an affinity membrane and into the bulk fluid at a rate significantly faster than it could diffuse from an affinity support particle and into the bulk fluid.

The relatively rapid elution rates which have been discovered to be possible with affinity membranes can be expected to improve both the yield of active protein recovered in affinity separations and the useful life of immobilized ligands in cases where ligand and/or ligate are sensitive to (e.g., denatured by) the harsh elution conditions that may be employed. Generally speaking, the extent of protein denaturation/deactivation suffered during elution can be expected to increase with both the harshness of the elution conditions and the time of exposure to such conditions. By eluting in as short a time as possible, retention of ligate bioactivity and/or ligand bioactivity can be maximized.

Two characteristic elution times can be identified that will be important to minimizing exposure of proteins to harsh elution conditions. The immobilized ligand will obviously be exposed to the eluent solution for the full duration of the elution step in the affinity purification cycle; this duration will include not only the time corresponding to the main elution step, but also that corresponding to other parts of the elution sequence such as the pre- and post-elution steps discussed above. Generally speaking, it is this total elution time that will be most pertinent to the matter of ligand denaturation. The same can be said for the last bit of ligate to be eluted from the affinity matrix; that is, it will be the total (combined) length(s) of the elution step(s) that will determine the extent of denaturation, if any, of that protein which is last to be eluted from the affinity support matrix.

A different characteristic elution time will be more pertinent to the matter of denaturation of the bulk of the protein which is eluted from the affinity matrix during the first part of the elution step. In particular, this portion of the eluted protein will be exposed to harsh elution conditions for a period of time not much longer than the residence time of fluid in the affinity support matrix during the elution step, which may be calculated from the ratio of membrane void volume to volumetric flowrate.

On average, then, protein being eluted from an affinity support will experience harsh elution conditions for some period of time intermediate between the residence time and the total elution time. It has been discovered that the use of affinity membranes makes it possible to keep both of these characteristic elution times very short, as compared to their corresponding values in affinity columns.

The rapidity of elution from affinity supports can also be measured in terms of a space velocity, that is, volumes of solution passed through the membrane matrix per unit volume and unit time. Whereas the affinity membranes of the present invention can be operated during elution at space velocities as high as about 15 to 20 reciprocal minutes (min.$^{-1}$), more conventional gel-type (e.g., crosslinked agarose) and silica based affinity columns are operated at space velocities of between about 0.05 to 0.5 min$^{-1}$ and 0.1 to 0.25 min$^{-1}$, respectively. For example agarose supports are typically operated at a space velocity of about 0.1 min$^{-1}$ and silica supports at about 0.2 min$^{-1}$.

Quenched Elution in Affinity Membrane Apparatus and Protein Purification Processes In certain situations, it will prove either necessary or desirable to employ a harsh and potentially denaturing buffer in the elution step; for example, the strength of ligand-ligate binding may be such that only harsh elution conditions (e.g., acidic pH values, as low as 1.5 to 2.0 in some instances or a high concentration of a chaotropic salt or other eluting solute) will suffice to bring about appreciable release of protein from the immobilized affinity ligand. In these cases, another method of operation of affinity membranes that minimizes the length of exposure of the eluted protein to these severe elution conditions can be employed. In particular, it has been found to be possible to operate an affinity membrane purification process in a "quenched elution" mode wherein, e.g., an acidic eluent is promptly neutralized or a high concentration of eluting solute is promptly reduced by dilution or other means, and protein denaturation is thereby minimized. This "quenched elution" aspect of the present invention can be realized via either one of two possible embodiments, which are discussed below in turn.

The first method for bringing about "quenched elution" with affinity membranes involves taking advantage of the rapid elution aspect of affinity membrane operation discussed above. In particular, the product stream produced during the main elution portion of the affinity purification cycle is rapidly brought into contact with a neutralizing solution capable of bringing the mixed streams to a near-neutral pH at which the eluted protein exhibits satisfactory stability. For example, if the elution buffer is highly acidic, the neutralizing solution may consist of an aqueous solution of a base or, preferably, a high-buffering-capacity solution at near-neutral pH.

The neutralizing buffer must be supplied at a flowrate sufficient to neutralize the acidic buffer components in the eluate. This mixing of low-pH eluate solution with neutralizing solution can be accomplished, for example, in a mixing tee located downstream of the affinity membrane module. Alternatively, neutralization of the low-pH eluate may be accomplished in the downstream product reservoir. The low-pH eluate solution may either be directed to a product reservoir tank fitted with pH control means (e.g., caustic or buffer supply lines, a pH meter, and appropriate control circuitry) or it may be directed into a product tank that already contains a neutralizing solution with ample buffering capacity. An apparatus such as that described above and in copending U.S. applications Ser. Nos. 07/265,061 and 07/428,263, can be modified for performing quenched elution. Such an apparatus would include a reservoir for the neutralizing solution, a pump for the neutralizing solution and/or a port on the lumen side of the affinity module for introducing the neutralizing solution.

Regardless of the detailed manner in which this mixing and neutralization of the eluate solution are accomplished, it is critical to obtaining the full benefit of the present invention that the time between eluting the target protein and neutralizing the solution containing it be kept to a minimum. It has been found that affinity membranes are ideal for realizing this objective, since their characteristic elution times, in particular, the total elution time and eluent residence time of affinity membranes, can be made extremely short relative to the corresponding parameters that describe the operation of affinity columns based on particulate or bead-type packings.

Yet a more elegant embodiment of this "quenched elution" aspect of the present invention involves neutralizing a harsh (e.g., acidic) elution buffer while the latter is still within the affinity membrane device. Where indicated, this "quenched elution" process can be conducted in place of the main elution step. This mode of affinity membrane operation permits even shorter and accordingly less destructive time lags between release of target protein and subsequent eluent neutralization; this is accomplished by feeding the neutralizing buffer directly to the lumens of the hollow fibers of an affinity membrane device.

In this embodiment, two process streams are simultaneously fed to the membrane device on opposite sides of the membrane contained within it, namely, the low-pH eluent and the neutralizing buffer ultimately to be brought into contact within it. A single product stream emerges from the module at near-neutral pH. Accordingly, time lags associated with hold-up of fluid within the affinity membrane module and associated tubing can be eliminated, since the protein-containing eluent solution mixes with neutralizing solution as soon as the former emerges from the wall (i.e., either the inner lumenal surface or the outer, shell-side surface) of the affinity fibers. By keeping the flowrate of neutralizing buffer fed to the module such that it is capable of neutralizing the entire transmembrane flux of the product solution, the length of exposure of eluted protein to harsh elution conditions can be kept equal to or even smaller than the residence time of eluent solution in the affinity membrane matrix, typically, just a few seconds.

In cases where high concentrations of a salt or other eluting solutes (e.g., sugars in the case of immobilized lectins) are used in the elution step, quenched elution techniques to rapidly reduce the concentration of such solutes e.g., by dilution, complexation, or other means can be used.

The present invention is further illustrated by the following examples, which are not intended to be limiting in any way.

EXAMPLES

Example 1

The ligate purified in this example is a murine monoclonal antibody (MAb) of the $IgG_{2a}$ subclass, produced by mammalian cell culture. The particular antibody employed, which has the property of selectively binding to a particular cell surface receptor, was under investigation for use as a therapeutic in the treatment of certain forms of cancer.

The monoclonal antibody was first loaded onto three protein A-containing affinity matrices at neutral pH, and then the conditions required for elution of the MAb from each support were determined. The following three affinity supports were tested in this fashion:

(1) Protein A Sepharose TM — a commercially available soft gel affinity chromatography matrix obtained from Pharmacia and characterized by a nominal bead diameter of about 60 to 140 microns and a static or equilibrium capacity for this monoclonal antibody of about 5.2–6.0 mg/mL gel bed volume;

(2) Protein A AvidGel F TM — another commercial bead-type product obtained from Bioprobe International and characterized by a particle diameter in the range of about 40 to 200 microns and a static capacity for this particular antibody of 5.9–6.2 mg/mL packed bed volume; and (3) a Protein A hollow-fiber affinity membrane module (1.5 mL device volume) prepared at Sepracor in substantially the same manner as described in prior copending U.S. application Ser. No. 07/258,406 and characterized by a static capacity for MAb uptake of about 4.8–6.0 mg/mL membrane matrix volume.

Protein A was immobilized onto the various supports using cyanogen bromide (CNBr) linking chemistry in the case of the Protein A Sepharose TM product and using fluoromethylpyridinium p-toluenesulfonate (FMP) linking chemistry in the cases of the Protein A AvidGel F TM product and the Protein A affinity membrane module. The Protein A Sepharose TM material was chosen for use in this study because it is one of the more commonly used affinity matrices, while the AvidGel F TM product was chosen for comparison in this study because it is bas d on the same FMP linking chemistry as used in the a.finity membranes.

The Sepharose TM and AvidGel F TM bead-type supports (based on polysaccharide and vinyl support chemistries, respectively) were packed into 0.5 mL columns— a volume identical to that of the membrane matrix in the affinity membrane device (i.e., the total volume occupied by the walls of the microporous hollow-fiber membrane in the module). A solution containing approximately 4 to 5 mg of the pure monoclonal antibody was loaded onto each support, corresponding to a loading of 8–10 mg/mL of packed bed or membrane matrix volume. Each of the affinity supports was essentially saturated with ligate.

Antibody was subsequently eluted from these matrices in a manner that permitted determination of differences in the relative strength (and thus "harshness") of the elution buffer required to displace a given fraction of antibody from each type of support. In particular, buffered solutions of decreasing pH were passed over each support in a stepwise fashion (with a nominal step size approximately 0.5 pH unit) and the amount of protein eluted at each pH was determined by measuring the absorbance of the effluent at 280 nm as a function of cumulative volume and then integrating under the curve. Elution flowrates of 1 mL/min and either 2.5 or 5 mL/min were employed with each elution step typically involving about 10–14 mL of elution buffer. The eluted protein appeared in the effluent as a series of peaks, with the approach of the effluent UV absorbance to a near-baseline value signalling a substantial decrease in the rate of protein elution from the support and near-completion of protein elution at a given pH value.

Results obtained in ths differential elution study are summarized in Table II. It can be seen that the bulk of the protein bound to the membrane was eluted at a less acidic pH than those from the two particulate supports, Sepharose TM and AvidGel F TM. For example, the largest amount of protein was eluted from the membrane at a pH slightly greater than 6, whereas maximal elution did not occur for the AvidGel support until the elution pH was a full pH unit lower. Similarly, the largest fraction of protein eluted from the Sepharose TM matrix at a pH value about 0.5 unit more acidic than the corresponding value for the affinity membrane. Viewed another way, about one-quarter to one-third of the monoclonal antibody was eluted from the affinity membrane before any significant quantity of protein was released from either of the bead-type affinity supports.

TABLE II

Cumulative Elution of Antibody as a Function of Elution pH and Support

| Type of Matrix | Flowrate | pH | Fraction Eluted (%) |
| --- | --- | --- | --- |
| Membrane (FMP) | 1 mL/min | 7.70 | 10.1 |
| | 1 mL/min | 7.20 | 24.2 |
| | 1 mL/min | 6.70 | 45.1 |
| | 1 mL/min | 6.10 | 79.8 |
| | 1 mL/min | 5.70 | 95.1 |
| | 1 mL/min | 5.00 | 98.0 |
| | 1 mL/min | 4.60 | 99.9 |
| Membrane (FMP) | 5 mL/min | 7.53 | 8.5 |
| | 5 mL/min | 7.12 | 22.0 |
| | 5 mL/min | 6.68 | 38.5 |
| | 5 mL/min | 6.10 | 76.2 |
| | 1 mL/min | 5.67 | 94.9 |
| | 1 mL/min | 5.02 | 100.0 |
| Sepharose TM (CNBr) | 1 mL/min | 6.60 | 17.0 |
| | 1 mL/min | 6.00 | 47.0 |
| | 1 mL/min | 5.60 | 79.0 |
| | 1 mL/min | 5.00 | 96.0 |
| | 1 mL/min | 4.60 | 100.0 |
| | 5 mL/min | 6.60 | 17.0 |
| | 5 mL/min | 6.00 | 45.0 |
| | 5 mL/min | 5.60 | 74.0 |
| | 5 mL/min | 5.00 | 96.0 |
| | 5 mL/min | 4.60 | 100.0 |
| AvidGel F TM (FMP) | 1 mL/min | 7.50 | 0.0 |
| | 1 mL/min | 7.00 | 0.2 |
| | 1 mL/min | 6.70 | 2.8 |
| | 1 mL/min | 6.10 | 26.1 |
| | 1 mL/min | 5.70 | 60.2 |
| | 1 mL/min | 5.10 | 99.5 |
| | 1 mL/min | 4.60 | 100.0 |
| | 2.5 mL/min | 7.60 | 0.0 |
| | 2.5 mL/min | 7.10 | 0.3 |
| | 2.5 mL/min | 6.60 | 3.6 |
| | 2.5 mL/min | 6.10 | 25.7 |
| | 2.5 mL/min | 5.67 | 60.2 |
| | 2.5 mL/min | 5.09 | 99.6 |
| | 2.5 mL/min | 4.62 | 100.0 |

Example 2

Based on the data in Example 1, it was expected that the affinity membrane device could be effectively eluted at pH 5.6, whereas elution of a protein A particulate column under those conditions was expected to result in poor recovery. This was tested experimentally by comparing the performance of a hollow-fiber affinity membrane module (1.5 mL device volume, 0.5 mL matrix volume) with a 5 mL protein A Sepharose TM column when both supports were eluted with 0.1M citrate buffer at pH 5.6.

Each support was first loaded with 200 mL of solution containing the same antibody employed in Example 1, but with the MAb present in clarified cell culture supernatant (as opposed to a solution of pure antibody as used in Example 1). Ten affinity purification cycles were performed with the membrane device, whereas a single cycle sufficed for the larger column. The amounts of protein product eluted from the membrane and particulate supports were determined by protein A HPLC.

It was found that 77% of the MAb taken up by the membrane was recovered in the pH 5.6 eluate, when the affinity membrane was operated at a total elution time of 110/sec cycle. An identical recovery was obtained when elution was performed at a more acidic pH of 3.0. In contrast, only 47% of the bound MAb was eluted from the Sepharose column at pH 5.6 during the 36-minute elution period. In order to elute an additional 28% of the target protein from the column, it proved necessary to reduce the pH of the buffer used to elute the protein A/Sepharose column to 3.0.

These experimental results indicate that a protein A membrane device can be eluted under milder conditions than those required for gel-type and porous bead supports. In situations where the ligand and/or ligate have limited stability at extremes of pH, this has important consequences both to the recovery or yield of the protein being purified as well as to the useful lifetime of the immobilized ligand.

Without wishing to be limited as to the underlying mechanism by which release of bound protein can be effected at mild elution conditions in affin:.y membrane purifications, it is possible to suggest a rationale for mild elution which is based on the reduced diffusional resistances that affinity membranes afford in the elution step. Protein elution can be regarded as a sequential two-step process:

1) a "chemical reaction" step involving the dissociation of some fraction of the bound protein from the immobilized ligand on the surface of the affinity matrix, followed by 2) a "physical" step involving diffusion of the free ligate away from the surface of the affinity matrix and into the bulk eluent stream flowing past the surface.

The dissociation step (1) produces a concentration of free protein at the surface of the ligand-immobilizing matrix that is somewhat higher than that in the bulk fluid. It is this surface-to-bulk-fluid concentration difference of free protein that provides the driving force for the subsequent diffusion step (2).

The local equilibrium between free and bound ligate at the surface of the affinity matrix will be recognized to be a function of pH (and perhaps other solution conditions). Typically, and specifically, for example, in the case of the protein A ligand the strength of biochemical binding is greatest at near-neutral pH values and is diminished at relatively acidic (or basic) pH values. (This is the basis for loading IgG onto protein A affinity supports at near-neutral pH and then eluting it therefrom at an acidic pH of about 3 or below, as described above). The local concentration of free ligate at the affinity matrix surface is thus seen to increase as the local pH at the surface is reduced.

Reducing the pH at the surface of the affinity matrix thus has the following effects on the sequential "reaction" and diffusion steps involved in the protein elution process:

1) reduced pH increases the extent of ligand-ligate dissociation, thereby increasing the local surface concentration of free ligate, and
2) this higher surface concentration increases the surface-to-bulk concentration-difference driving force and hence the rate of diffusion of free ligate into the bulk eluent.

Now it will be recognized that the diffusion flux of free ligate from the surface will be directly proportional to the surface-to-bulk ligate concentration difference, and it will be inversely proportional to the mass transfer resistance to diffusion. It follows that the rate of elution of protein from the surface may thus be enhanced either by increasing the surface concentration of free ligate by employing a harsh (e.g., acidic) elution buffer and/or by reducing the diffusional resistance, which in turn is approximately inversely proportional to the square of the characteristic surface-to-bulk diffusion distance as discussed above. Where affinity membranes are employed, this characteristic diffusion distance is typically a fraction of a micron as opposed to the values of microns or tens of microns that are typical of particulate affinity supports.

Thus, where the objective is to maintain a given elution rate from both membrane and particulate type affinity supports, a smaller membrane surface concentration of free ligate suffices to produce the same surface-to-bulk diffusion flux (and therefore elution rate) than that which would be required to achieve the same elution flux from an affinity bead or particle. Accordingly, the elution conditions required to bring about a certain elution rate can be expected to be milder in the case of affinity membranes as opposed to affinity columns, consistent with the experimental results set forth in Example 1.

Example 3

The ligate purified in this example was macrophage colony stimulating factor or MCSF, a glycoprotein; this was accomplished using immobilized lentil lectin (LL) from lens culinaris as the affinity ligand and the monosaccharide, in particular, a methyl-alpha-D-glucopyranoside or $\alpha$MG, as a specific eluent. In conventional processes for the affinity purification of MCSF, the lentil lectin ligand is bound to Sepharose ™ gel supports, which exhibit dynamic capacities of about 0.8 mg/mL of bed. In the affinity membrane purification process of the present invention, the lentil lectin was immobilized on 1.5 mL (0.5 mL membrane matrix volume or MMV) and 30 mL (10 mL MMV) hollow-fiber affinity membrane modules using FMP linking chemistry as described above and in the previously cited copending patent applications. Approximately 1 to 2 mg of lentil lectin were immobilized per mL of membrane matrix volume, leading to dynamic capacities for MCSF uptake in the range of 3 to 4 mg/mL MV and static or equilibrium capacities of about 10 mg/mL.

The lentil lectin membrane modules were loaded with a solution of MCSF containing 0.02M Tris buffer, 0.1M NaCL, and 0.1% Tween at pH 7.4. Loading conditions and flowrates were typically chosen to provide good capture efficiencies for MCSF. For instance, in one experiment, 400 mL of MCSF-containing solution were processed in four cycles, each processing 100 mL at a filtrate flowrate of 2.0 mL/min. After loading, the membrane matrix was washed with a buffer containing only 0.02M Tris and 0.1% Tween at pH 7.4.

The composition of the solutions employed in the subsequent elution steps was varied in a series of experiments in an attempt to determine how low a concentration of the $\alpha$MG displacing sugar would prove effective in eluting MCSF from the affinity membrane matrix. In these experiments, the affinity membrane module was first loaded with MCSF to saturation (about 10 mg/mL MV). In all cases, the elution buffers contained 0.5M NaCl, 0.02M Tris and 0.1% Tween at pH 7.4. However, the concentration of $\alpha$MG in the elution solution was varied from 0.0 to 0.4M as shown in Table III. It can be seen that $\alpha$MG concentrations significantly less than 0.4M sufficed to displace a high fraction of the MCSF from the lentil-lectin affinity membrane. Concentrations of $\alpha$MG of about 0.05 to 0.10M are preferred in a practical affinity membrane process for MCSF purification.

TABLE III

EFFECT OF $\alpha$MG CONCENTRATION ON ELUTION OF MCSF FROM LENTIL LECTIN AFFINITY MEMBRANE

| $\alpha$MG Concentration in Eluent* (M) | Fraction MCSF Eluted (%) |
|---|---|
| 0.0 | 86.6 |
| 0.05 | 94.9 |
| 0.1 | 98.7 |
| 0.2 | 100. |
| 0.4 | 100. |

*Elution buffers also contain 0.5 M NaCl, 0.02 M Tris, and 0.1% Tween at pH 7.4

In control experiments conducted with lentil lectin-Sepharose columns, it was found that significantly higher concentrations of $\alpha$MG—in particular, 0.4M—were required to elute MCSF from the Sepharose gel support at comparable recoveries. In view of the reported increase in the rate of lectin leaching associated with the use of high concentrations of displacing sugars in the elution step of similar affinity purifications (Walzel et al., op cit.), it is reasonable to believe that the milder elution conditions (i.e., lower $\alpha$MG concentration) which proved satisfactory in the affinity membrane purification process should lead to a longer useful lifetime of the membrane-immobilized lentil lectin ligand.

EXAMPLE 4

A murine monoclonal antibody (MAb) of the IgG$_{2a}$ subclass (the same antibody used in Example 1) was purified from cell culture supernatant containing 5% fetal calf serum supplement (and clarified by 0.2μ microfiltration) using an affinity membrane module activated by attachment of protein A to its interior porewall surface area as described above and in the copending U.S. patent application previously cited and incorporated herein. The feed solution contained 177 mg/L of monoclonal antibody. The affinity membrane module (nominally 30 mL total device volume) contained 10 mL of ligand-activated membrane matrix volume with a static capacity for MAb uptake of about 7 mg/mL.

Purification cycle parameters and results are summarized in Table IV. A total of 1.7 liters of MAb-containing feed solution were processed in the course of 10 cycles, with the duration of each cycle being 3.5 minutes. A total of 30 mg of MAb were loaded onto the affinity membrane during each cycle, with 26 mg (or about 87%) of this ligate subsequently being recovered in the eluate at a product purity of 88% as determined by protein A HPLC. Particularly germane to the practice of the present invention are the two characteristic elution times at which the affinity membrane system was successfully operated in this experiment; both are very short as compared to elution times typical of column chromatographic operations. In particular, the total elution time for the pre-, post-, and main elution steps in each purification cycle was limited to 48 seconds, with product being collected only during the 29-second-long main elution step.

TABLE IV
PURIFICATION OF MONOCLONAL ANTIBODY FROM CELL CULTURE SUPERNATANT UNDER RAPID ELUTION CONDITIONS

PURIFICATION CYCLE BREAKDOWN:

| Step | Time (sec) | Volume (mL) |
| --- | --- | --- |
| Load | 47 | 170 |
| Wash/Flush | 47 | 145 |
| Pre-Elute | 3 | 10 |
| Main Elute | 29 | 87 |
| Post-Elute | 16 | 48 |
| Regenerate | 68 | 185 |
| Total: | 210 | 645 |

PURIFICATION CYCLE SUMMARY:

| | Per Cycle | Total |
| --- | --- | --- |
| Volume processed (mL) | 170 | 1700 |
| MAb processed (mg) | 30 | 300 |
| MAb recovered (mg) | 26 | 258 |
| Time elapsed (min) | 3.5 | 35 |

The second important characteristic elution time, namely, the residence time of eluent during the elution step, was only 2.5 seconds in this experiment. This latter value may be calculated from the membrane matrix volume (10 mL), the membrane porosity (75%), and the eluent flowrate (160 mL divided by 53 sec or 3.0 mL/sec) using the following simple relationship:

eluent residence time = (10 ml) × (0.75)/(3.0 mL/sec)

eluent residence time = 2.5 seconds

As a consequence of rapid elution from the affinity membrane and the relatively short total elution and residence times associated with this process, the length of time to which potentially sensitive ligand and ligate proteins must be exposed to harsh elution conditions can be minimized. Accordingly, retention of protein bioactivity can be maximized in affinity membrane methods and apparatus.

EXAMPLE 5

Another monoclonal antibody of the $IgG_{2a}$ subclass (different from the antibody purified in Examples 1, 2 and 4) was purified using a protein A-activated affinity membrane module (30 mL device volume, 10 mL matrix volume) and substantially the same purification cycle as described in Example 4. A volume of 284 mL of feed solution containing monoclonal antibody at a titer of 84.2 mg/L was processed. Wash and regeneration buffers consisted of phosphate buffered saline at pH 8.0; 0.1M citrate buffer at pH 3.0 was used to elute the target protein from the membrane support.

Table V summarizes the volumes of fluids generated at various points in the purification cycle, as well as the concentration, amounts, and fractional recoveries of antibody in each fraction as determined by protein A HPLC. The overall length of the elution portion of the purification cycle was 33 seconds, corresponding to a main elution time of 20 seconds (step 7) and pre- and post-elution times of 3 and 10 seconds, respectively, for steps 6 and 8. The residence time of elution buffer in the membrane matrix was calculated as above to be 2.5 seconds. Despite these extremely short total elution and residence times, it can be seen from Table IV that 79% of the target protein was eluted from the membrane during the very rapid 20-second-long main elution step.

TABLE V
PURIFICATION OF A MONOCLONAL ANTIBODY USING RAPID ELUTION

Purification Program

| Step | Time (sec) |
| --- | --- |
| 1 | 7 |
| 2 | 15 |
| 3 | 7 |
| 4 | 30 |
| 5 | 5 |
| 6 | 3 |
| 7 | 20 |
| 8 | 10 |
| 9 | 30 |
| 10 | 20 |

| Fluid | Steps(s) | Volume (mL) |
| --- | --- | --- |
| Feed/Filtrate | 1 | 284 |
| Product | 7 | 63 |
| Shell Wash/Flush | 2, 5, 9 | 163 |
| Lumen Wash/Flush | 3-4, 6, 8 | 145 |
| Lumen Regenerate | 10 | 79 |

| Fluid | MAb Conc. (mg/L) | Amount MAb (mg) | Recovery (%) |
| --- | --- | --- | --- |
| Feed | 84.2 | 23.9 | 100.0 |
| Filtrate | 6.0 | 1.7 | 7.1 |
| Product | 298. | 18.8 | 79. |
| Shell | 3.3 | 0.5 | 2.3 |
| Lumen Wash | 9.1 | 1.3 | 5.5 |
| Lumen Regen. | 2.2 | 0.2 | 0.7 |

EXAMPLE 6

Yet another monoclonal antibody of the $IgG_{2a}$ subclass, this one produced in an attached-cell bioreactor as opposed to suspension culture, was purified using the protein A affinity membrane apparatus described in the preceding examples. The purification program employed was identical to that presented at the top of Table IV. A volume of 1150 mL of feed solution containing monoclonal antibody at a titer of about 72 mg/L was processed in this manner in four purification cycles.

As before, wash and regeneration buffers consisted of phosphate buffered saline at pH 8.0; 0.1M citrate buffer at pH 3.0 was used to elute the target protein from the membrane support.

Table VI summarizes the volumes of fluids generated at various points in the purification cycle, as well as the concentrations, amounts, and fractional recoveries of antibody in each fraction as determined by protein A HPLC. The overall length of the elution portion of the purification cycle was 33 seconds, corresponding to a main elution time of 20 seconds (step 7) and pre- and post-elution times of 3 and 10 seconds, respectively, for steps 6 and 8. The residence time of elution buffer in the membrane matrix was calculated as above to be 2.5 seconds. Despite these extremely short total elution and residence times, it can be seen from Table V that nearly 97% of the target protein was eluted from the membrane during the very rapid 20-second-long main elution step.

TABLE VI
PURIFICATION OF A MONOCLONAL ANTIBODY USING RAPID ELUTION

| Fluid | Steps(s) | Volume (mL) |
| --- | --- | --- |
| Feed/Filtrate | 1 | 1154 |
| Product | 7 | 255 |
| Shell Wash/Flush | 2, 5, 9 | 649 |
| Lumen Waste (Wash/Flush/Regen.) | 3-4, 6, 8, 10 | 898 |

| Fluid | MAb Conc. (mg/L) | Amount MAb (mg) | Recovery (%) |
| --- | --- | --- | --- |
| Feed | 71.6 | 82.6 | 100.0 |
| Filtrate | 0.8 | 0.9 | 1.1 |
| Product | 313. | 79.8 | 96.6 |
| Shell | 1.5 | 1.0 | 1.2 |
| Lumen Waste | 3.9 | 3.5 | 4.2 |

EXAMPLE 7

A protein-A activated affinity membrane module (1.5 mL device volume, 0.5 mL membrane matrix volume) was fed a solution containing human IgG as the target protein in an affinity membrane apparatus modified so as to permit quenched elution to be carried out in the manner shown in the Figure, with the fluid streams following flow paths designated by the boldface lines and arrows. After loading, the module was washed until the absorbance of the effluent was essentially zero. Next, the shell-side compartment of the affinity membrane module was flushed with elution buffer (0.1M citrate buffer at pH 3.0), and "quenched elution" was subsequently carried out. This was accomplished by passing the acidic elution buffer through the walls of the IgC-loaded affinity hollow-fiber membrane at a flowrate of 10 mL/min, while a neutralizing solution containing 1M Tris base was pumped into the lumen inlet port at a flowrate of 3.5 mL/min.

A neutralized product-containing solution at pH 8.0 emerged from the lumen outlet at the opposite end of the affinity membrane module. This product was collected and tested for human IgG by protein A HPLC. The amount of product recovered was 4.3 mg.

The membrane was subsequently eluted without quenching. No product could be detected in the eluate in this experiment, indicating that the quenched elution procedure had brought about essentially complete desorption and recovery of bound IgG.

Equivalents

Those skilled in the art will recognize or be able to ascertain using no more than routine experimentation, many equivalents to the specific embodiments of the invention described herein. Such equivalents are intended to be encompassed within the scope of this invention.

We claim:

1. A method for eluting a pH-sensitive ligate from a ligate-loaded membrane comprised of the ligate associated with an immobilized ligand, the ligand being bound to a microporous membrane, said method comprising the steps of:
    a) delivering an acidic or basic eluent to a first side of the ligate-loaded membrane and causing said eluent to pass transversely therethrough to a second side of the membrane, wherein said eluent dissociates the ligate from the immobilized ligand, whereby a solution of eluted ligate in eluent is obtained; while simultaneously
    b) delivering a quenching solution to the second side of the membrane, such that the eluted ligate solution is neutralized to a pH of from about 6 to about 8.5 upon emerging from the second side of the microporous membrane.

2. A method of claim 1 wherein the pH-sensitive ligate is associated with a bacterial $F_c$ receptor protein and the immobilized ligand comprises a bacterial $F_c$ receptor protein.

3. A method of claim 2 wherein the pH-sensitive ligate comprises an immunoglobulin.

4. A method of claim 2 wherein the immobilized ligand is selected from the group consisting of Protein A, Protein G and hybrids of Protein A and Protein G.

* * * * *